United States Patent [19]

Webster

[11] 4,422,760
[45] Dec. 27, 1983

[54] OPTICAL ANALYZING INSTRUMENT HAVING VIBRATING TROUGH

[75] Inventor: Donald R. Webster, Laurel, Md.

[73] Assignee: Pacific Scientific Instruments Company, Anaheim, Calif.

[21] Appl. No.: 236,580

[22] Filed: Feb. 20, 1981

[51] Int. Cl.³ .................. G01N 21/01; G01N 21/55
[52] U.S. Cl. .................................. 356/244; 250/576; 356/445
[58] Field of Search ............... 356/36, 244, 418, 445; 250/573, 574, 576

[56] References Cited

U.S. PATENT DOCUMENTS 4,154,533  5/1979  Levine ............................. 250/574

FOREIGN PATENT DOCUMENTS 171134  11/1966  U.S.S.R. ............................. 356/445

*Primary Examiner*—Vincent P. McGraw
*Attorney, Agent, or Firm*—Lane, Aitken & Kananen

[57] ABSTRACT

An instrument for optically measuring and analyzing samples of particulate material includes a chute for conveying the samples through a light beam by which the measurements are made and a trough positioned at the bottom of the chute. The trough supports a column of the particulate material in the chute and acts as a gate to prevent the particulate material from flowing out of the chute. The trough is mounted on a vibrator and during the measurement operation vibrates to cause the particulate material to flow out of the chute. When vibrating, the trough transmits vibrations up through the column of particulate material in the chute to maintain the column in a free flowing condition and to prevent bridging.

7 Claims, 3 Drawing Figures

OPTICAL ANALYZING INSTRUMENT HAVING VIBRATING TROUGH

BACKGROUND OF THE INVENTION

In U.S. Pat. No. 4,040,747 to Donald R. Webster, issued Aug. 9, 1977, there is disclosed a relatively low cost instrument for measuring and analyzing the optical properties of organic materials to determine the percentages of certain constituents of the test materials. This instrument was developed to satisfy a need for a low cost instrument to rapidly determine the moisture, oil and protein content in produce and grain products. In the instrument disclosed in the patent, a source of wide-band infrared light is positioned to illuminate a sample through a filter assembly in which interference filters are arranged in the form of a paddle wheel mounted for rotation about an axis. As the filter wheel rotates, each filter is brought successively into the infrared light beam. As each filter is moved through the light beam by the filter wheel, the angle of incidence of the light beam on the filter changes and this changes the wavelength transmitted through the filter. Moreover, each filter provides a different range of wavelengths. By detecting the amount of reflection at selected specific wavelengths and the relationships of these reflectivities, the oil, protein and water content of the sample can be accurately and quickly determined.

U.S. Ser. No. 45,089, filed June 4, 1979, discloses an instrument of the type disclosed in the Webster patent, but in which the grinding is carried out automatically in the instrument at the time the measurement is made. In the invention disclosed in the application, a grinder is provided on the instrument with a hopper to hold grain and to introduce it into the grinder. A plate blocks the bottom of the hopper from the grinder so that the hopper may be filled with grain prior to a measuring operation. A reflectivity standard is positioned in the path of the infrared rays prior to each measurement to automatically calibrate the instrument. To initiate operation of the instrument, the reflectivity standard is pivoted out of the path of the infrared light. This action automatically energizes the grinder motor. Then, after a two-second delay to permit the grinder motor to get up to speed, grain is permitted to flow from the hopper into the grinder and the ground grain flows into a chute, the bottom of which is arranged to receive the infrared light passing through the filter wheel. The bottom of the chute is closed by an impeller to remove the grain from the chute. After a delay of 5 seconds, sufficient for the chute to fill up, the impeller is rotated to begin to move the grain out of the bottom of the chute. At this time, the instrument begins to make measurements as the grain in the chute moves through the infrared beam. This provides an automatic averaging from the sample being analyzed.

SUMMARY OF THE INVENTION

The present invention provides an instrument of the type disclosed in the Webster application, but in which the impeller is replaced by a vibrating trough positioned at the bottom of the chute. The vibrating trough acts as a conveyor to move the analyzed grain away from the chute. When the vibrator is off, the trough serves as a gate to stop the flow of grain. The vibrating trough also performs as an agitator by sending vibrations through the grain in the trough and up through the column of grain positioned in the chute, thereby preventing any clogging of grain in the chute. Thus, the column of grain in the chute moves downwardly in a uniform manner and at a constant rate, so that the measurements made as the grain passes through the infrared beam are more precise.

BRIEF DESCRIPTION OF THE DRAWINGS

FIG. 3 is a side view in elevation of the instrument of the invention shown in partial section through the chute and the vibrating through.

DESCRIPTION OF THE PREFERRED EMBODIMENT

Figure 1:
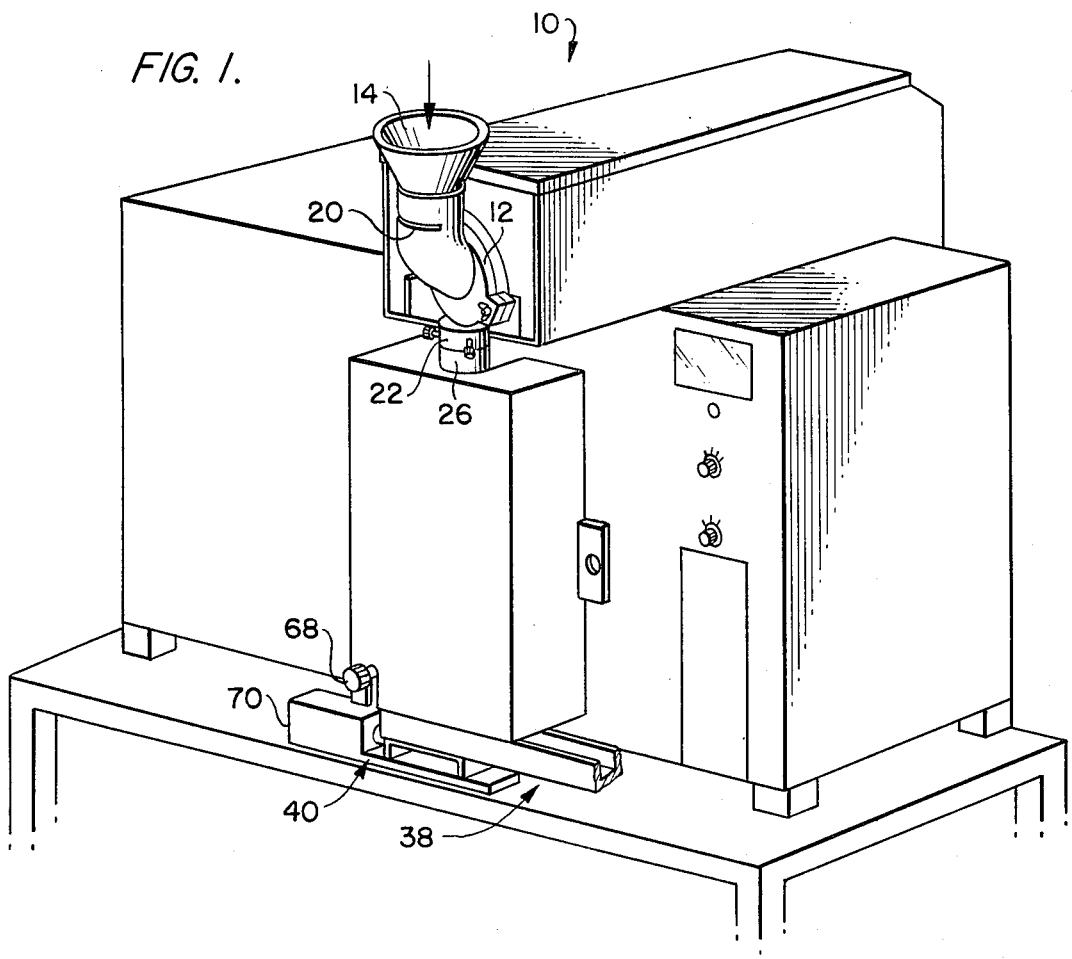
FIG. 1 is a perspective view of the grain analyzing instrument of the present invention.
Figure 2:
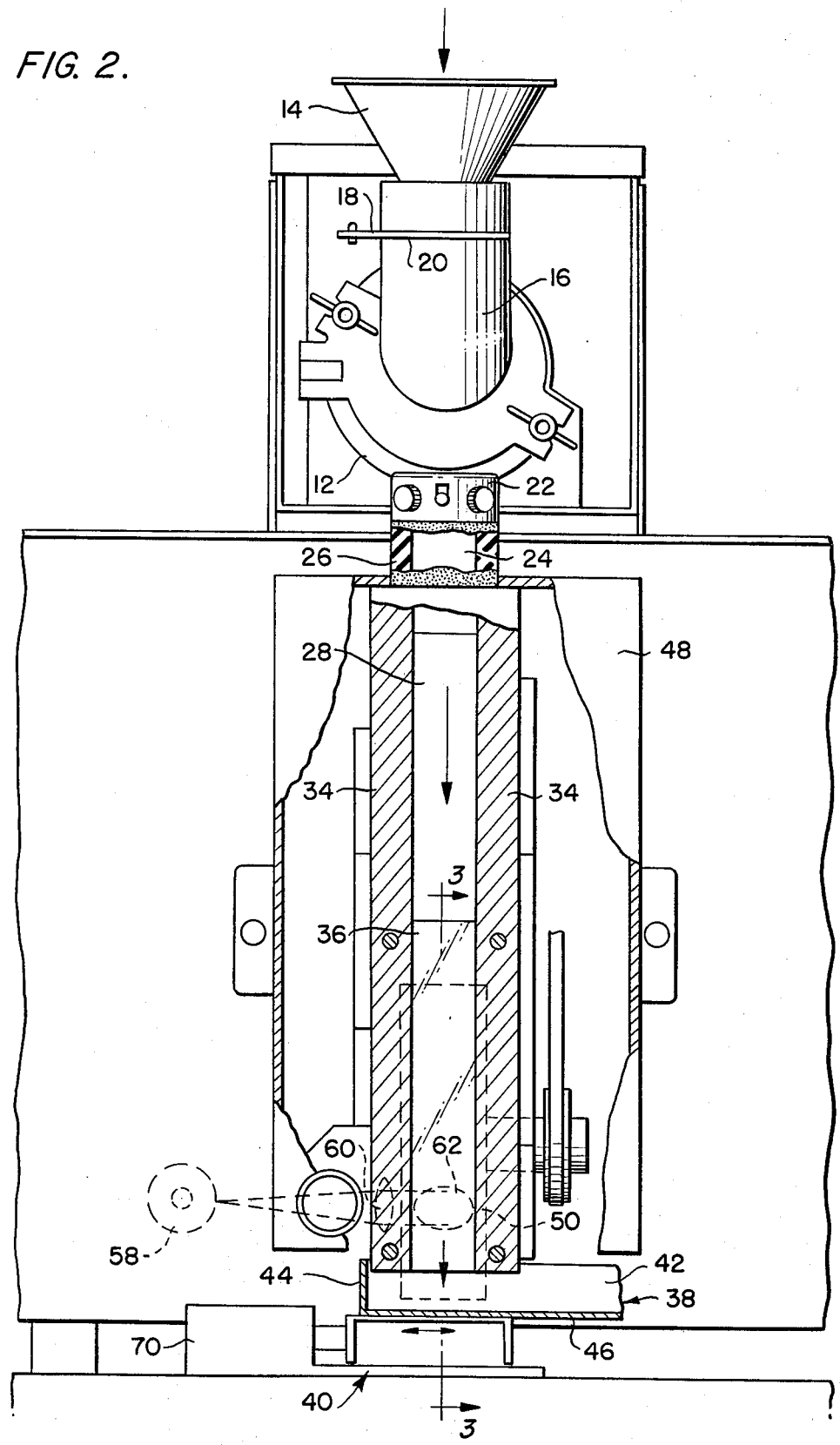
FIG. 2 is an enlarged front elevational view of the vibrating trough in position under the chute of the grain analyzing instrument.

As shown in FIGS. 1 and 2, the grain analyzing instrument of the present invention, referred to generally by the numeral 10, comprises a grinder 12 which is driven by a motor (not shown) and is adapted to receive grain for grinding from a hopper 14. The hopper 14 communicates with the input port to the grinder 12 through a conduit 16, which can be selectively closed by a plate 18 pivoting in a slot 20 formed in the wall of the conduit 16. The plate 18, which is referred to as a "grain gate", pivots between the position shown in FIGS. 1 and 2, in which the plate 18 blocks the conduit 16, and a position in which the plate 18 is pivoted out of the conduit 16, thereby allowing the flow of grain therethrough. The pivoting of the plate 18 is controlled by a rotary solenoid (not shown). The grinder 12 and its operation are described in more detail in Ser. No. 45,089, filed on June 4, 1979.

Figure 3:
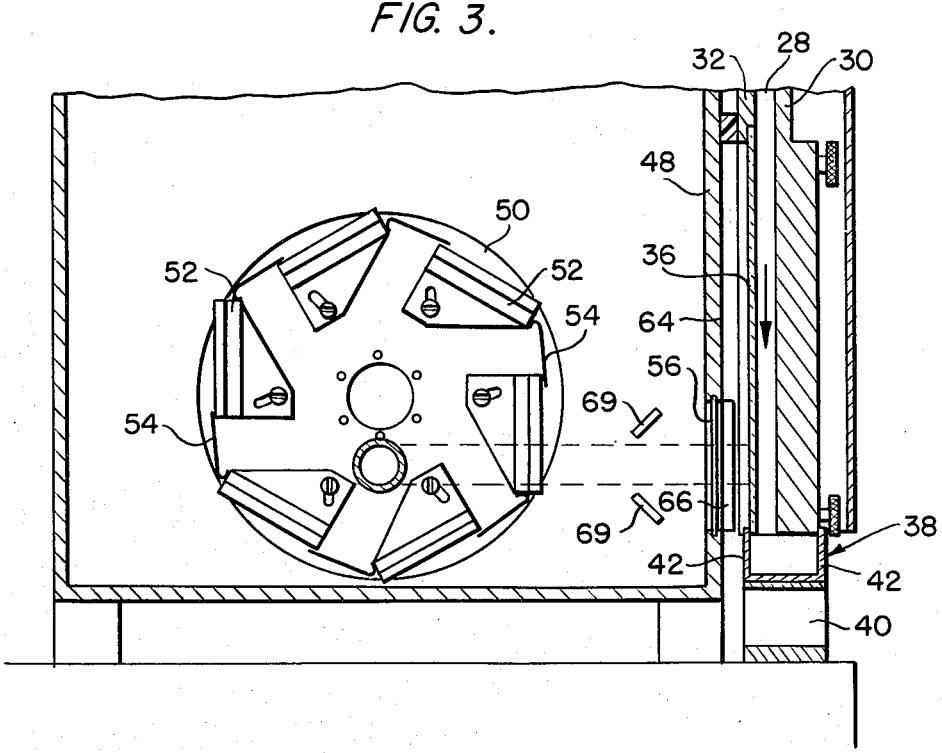

As best shown in FIGS. 2 and 3, grain ground by the grinder 12 exits from the grinder 12 through an exit port 22 at the bottom of the grinder 12 into a passageway 24 formed in a rubberized connector 26. The passageway 24 connects with a vertical chute 28 defined by front and back vertical walls 30 and 32, respectively, and side walls 34 to have a rectangular cross section. A window formed by an infrared light transmitting pane 36 is formed in the back wall 32 at the bottom of the chute 28. A trough 38 is positioned at the bottom of the chute 28 and is mounted on a vibrator 40 for imparting vibrations to the trough 38 and the material contained therein. The trough 38 includes a pair of side walls 42 extendng up along the outer surfaces of the front and back vertical walls 30 and 32, a rear wall 44 extending upwardly adjacent one of the side walls 34 of the chute 28 and a bottom wall 46, thereby defining a U-shaped channel having one closed end and one open end. The trough 38 may be inclined slightly so that its open end is lower than its closed end to aid the vibrator 40 in moving the grain.

The chute 28 and the passage way 24 up to the exit port 22 of the grinder 12 are formed to define flush inner side walls, or at least side walls having no ledges facing upward or against the direction of grain travel to help prevent bridging or clogging of the grain.

The front and back walls 30 and 32, the side walls 34 and the window 36 comprise a chute assembly which is mounted on the inner casing 48 in an easily removable manner.

As is illustrated in FIG. 3, contained within an inner casing 48 of the grain analyzing instrument 10, behind the window 36, is a filter wheel 50, which may be the same as that disclosed in U.S. Pat. No. 4,082,464, issued Apr. 4, 1978 to Donald R. Webster. The filter wheel 50 comprises a plurality of infrared interference filters 52 generally circumferentially arranged within the rim of the wheel. Attached at the circumference of the filter wheel 50 between adjacent filters 52 are opaque vanes 54. A window 56 is provided in the front wall of the inner casing 48 in alignment with the window 36. An infrared light source 58 (FIG. 2) directs an infrared beam parallel to the rotational axis of the wheel 50 and through a lens 60 into a mirror 62 mounted at an angle near the center of the wheel 50. The infrared beam is reflected by the mirror 62 radially out from the center of the wheel 50 through the window 56 and the window 36. The filter wheel 50 is arranged to rotate the filters 52 into the beam of infrared light so that the beam of light passes through the filters 52 successively. In addition, the rotation of the wheel 50 continuously changes the angle of inclination of each filter 52 as it passes through the beam of light, thereby continuously changing the narrow band of wavelengths transmitted by each filter 52. The filters 52 are selected to each transmit a different range of wavelengths to detect by reflectivity the constituent oil, water and protein in a grain sample. The opaque vanes 54 periodically interrupt the beam of light for purposes of zeroing the instrument in the manner disclosed in U.S. Pat. No. 3,861,788, issued to Webster on June 21, 1975.

As best shown in FIG. 3, there is a space 64 defined between the window 36 and the front wall of the inner casing 48 in which a standard arm 66 can pivot. Mounted on the backside of the arm 66 on the side adjacent to the front wall of the inner casing 48 and the window 56 is a procelain disc. The arm 66 can be pivoted by rotating a knob 68 extending from the front of the grain analyzing instrument 10 (FIG. 1). When the arm 66 is pivoted to a position in which the procelain disc is between the windows 36 and 56, light from the source 58, after passing through the window 56, is reflected from the procelain disc back through the window 56 to photocells 69 positioned to detect light reflected back through the window 56. The procelain disc serves as a standard of reflectivity to automatically calibrate the instrument in the manner described in U.S. Pat. No. 4,040,747 to Webster, in which a Telfon disc is used as the standard of reflectivity. The procelain disc serves the same purpose as the Teflon disc in the Webster patent.

The arm 66 can be pivoted upwardly to a position in which light from the source 58, after being filtered by the filter wheel 50, can pass through both windows 56 and 36 into the chute 28 to impinge upon grain in the bottom of the chute 28. The filtered infrared light will then be reflected back through the windows 36 and 56 to the photocells 69.

The vibrator 40 on which the trough 38 is mounted includes a casing 70 which can be affixed to the grain analyzing instrument 10 by means of a mounting plate or bracket, or can be supported by the surface supporting the grain analyzing instrument 10. The sides 42 of the trough 38 which extend upwardly along the front and back vertical walls 30 and 32 of the chute 28 do not engage the chute, so that only the column of grain within the chute 28, not the chute itself, is vibrated by the vibrating through 38. A container may be positioned under the open end of the trough 38 to collect the grain which is discharged. When the trough 38 is vibrating, the vibrations are transmitted through the grain resting in the trough 38 upwardly into the column of grain within the chute 28, thereby maintaining the grain in a fluent, free-flowing condition. Thus, through the action of the vibration and the influence of gravity, the grain in the chute 28 of the instrument 10 is moved uniformly downward through the chute 28, along the trough 38 and into the container. When the vibrator 40 is not operating, the grain in the trough 38 remains in the trough 38, and so the column of grain in the chute 28 is blocked from movement. Thus, the trough 38 acts as a gate for the chute 28 when the trough 38 is not vibrating.

To operate the system, the instrument 10 is initially turned on, in which condition a motor (not shown) will continuously drive the filter wheel 50 at a fixed rate, and the infrared light source 58 will direct a light beam through the filters 52 on the filter wheel 50 and through the window 56. The arm 66 will be in a position between the windows 56 and 36, so that the infrared beam will be reflected back from the procelain standard to the photocells 69. In response to the resulting signal produced by the photocells 69, the instrument will be automatically calibrated in the manner described in U.S. Pat. No. 4,040,747. The instrument 10 has a control system which operates in the manner of the control system of the aforementioned Ser. No. 45,089. The plate 18 closes off the conduit 16, so that grain may be loaded into the funnel 14. To initiate a measurement operation, the operator moves the arm 66 to its upper, non-obstructing position, which causes energization of the grinder motor. After a short time delay, the rotary solenoid is energized to open the gate 18 and allow the grain to be fed to the grinder 12. The grinder 12 then begins to grind the grain and direct it into the chute 28. Then, after another short time delay sufficient to let the bottom of the chute 28 fill up with ground grain at least past the top of the window 56, the vibrator 40 is energized to begin to vibrate the trough 38. As a result, the vibrating trough 38 removes the ground grain from the bottom of the chute 28 and vibrates the column of grain in the chute 38, thereby assuring that the ground grain in the chute 28 moves past the window 56 in a continuous stream. As the grain is being moved past the window 56, infrared light from the soucre 58 passing through the filters 52 of the filter wheel 50 impinges upon the grain and is reflected to the photocells 69, so that measurements of the constituents of the ground grain can be made in the manner described in U.S. Pat. No. 4,040,747. When the measurement is completed, the arm 66 falls back down between the windows 36 and 56, and the plate 18 returns to its closed position. Then, after a time delay selected to insure that the grinder 12 and the chute 28 are exhausted of the grain samples, the grinder 12 is de-energized and the vibrator 40 is de-energized to return the system to a condition ready to make the next grain measurements.

The instrument according to the present invention has been described as making measurements on grain samples. It will be apparent that the invention can be applied to other comminutable products to make analysis measurements. Other modifications may be made to the above-described preferred embodiment of the invention without departing from the spirit and scope of the invention, which is defined in the appended claims.

What is claimed is:

1. An analyzing instrument for analyzing samples of particulate material comprising a chute for receiving the samples of particulate material, the chute having a window therein, means positioned at the bottom of the chute for supporting a column of particulate material in the chute, for vibrating the column of particulate material to maintain the material in a freely flowing condition and for removing the particulate material from the chute, and measuring means for making optical measurements on the sample in the chute through said window as the particulate material moves past the window.

2. The analyzing instrument of claim 1 wherein the means for supporting, vibrating and removing the particulate material comprises a vibrating member.

3. The analyzing instrument of claim 2 wherein the vibrating member is a trough.

4. The analyzing instrument of claim 3 wherein the trough includes a closed end, an open end and sides extending upwardly above the bottom of the chute.

5. The analyzing instrument according to claim 1 wherein the instrument further comprises a grinder for grinding material to produce the samples of particulate material.

6. The analyzing instrument according to any one of the claims 1–5 wherein the particulate material comprises ground grain.

7. The analyzing instrument according to claim 1, wherein the interior cross-sectional dimensions of said chute are substantially constant at least along a portion of said chute between a point adjacent said window and said bottom.

* * * * *